United States Patent [19]

Abramson

[11] 4,166,450

[45] Sep. 4, 1979

[54] DEVICE AND PROCEDURE FOR COLLECTING A SUCCESSION OF INTRAVENOUS BLOOD SAMPLES

[75] Inventor: Harvey J. Abramson, New York, N.Y.

[73] Assignee: Metatech Corporation, Northbrook, Ill.

[21] Appl. No.: 817,929

[22] Filed: Jul. 22, 1977

[51] Int. Cl.² .............................................. A61B 5/14
[52] U.S. Cl. .................................................. 128/764
[58] Field of Search ............... 128/2 F, 218 R, 218 G, 128/216, 272, DIG. 5

[56] References Cited

U.S. PATENT DOCUMENTS

| | | | |
|---|---|---|---|
| 2,742,041 | 4/1956 | Lipari | 128/218 R |
| 3,159,159 | 12/1964 | Cohen | 128/2 F |
| 3,433,216 | 3/1969 | Mattson | 128/2 F |
| 3,494,352 | 2/1970 | Russo et al. | 128/2 F |
| 3,659,587 | 5/1972 | Baldwin | 128/2 F |
| 3,817,240 | 6/1974 | Ayres | 128/2 F |
| 3,965,889 | 6/1976 | Sachs | 128/2 F |
| 4,106,497 | 8/1978 | Percarpio | 128/2 F |

FOREIGN PATENT DOCUMENTS

| | | | |
|---|---|---|---|
| 1278387 | 10/1961 | France | 128/2 F |
| 1288383 | 2/1962 | France | 128/2 F |
| 1472049 | 1/1967 | France | 128/272 |
| 1260109 | 1/1972 | United Kingdom | 128/218 G |

Primary Examiner—Lee S. Cohen
Attorney, Agent, or Firm—Leydig, Voit, Osann, Mayer & Holt, Ltd.

[57] ABSTRACT

A blood sample collection device and procedure which employs a series of pre-evacuated rubber-capped vials for the drawing of successive samples. A hollow cylindrical carrier is used consisting of two cups which are integral base-to-base defining a main chamber and a mid-chamber. A soft rubber disc encloses the mid-chamber and defines an antechamber communicating with an intravenous needle. A piston carrying a double-ended auxiliary needle is slideable endwise in the mid-chamber. The antechamber is enclosed by transparent material such as plastic and is of such size as to admit only a trace of blood through the intravenous needle under venous pressure before the vial is connected, the blood in the antechamber serving as a visual telltale informing the user that the needle is in the lumen of the vein. The main chamber is laterally offset from the mid-chamber and antechamber, enabling the intravenous needle to be inserted at a shallow penetration angle notwithstanding the relatively large diameter of the main chamber and further insuring that the vial cap is penetrated in a random eccentric position. The vial is distinguished by use of an extensive rubber diaphragm held in place by screw-on cap which provides a reliable seal while permitting subsequent opening with only light manual twisting force.

3 Claims, 5 Drawing Figures

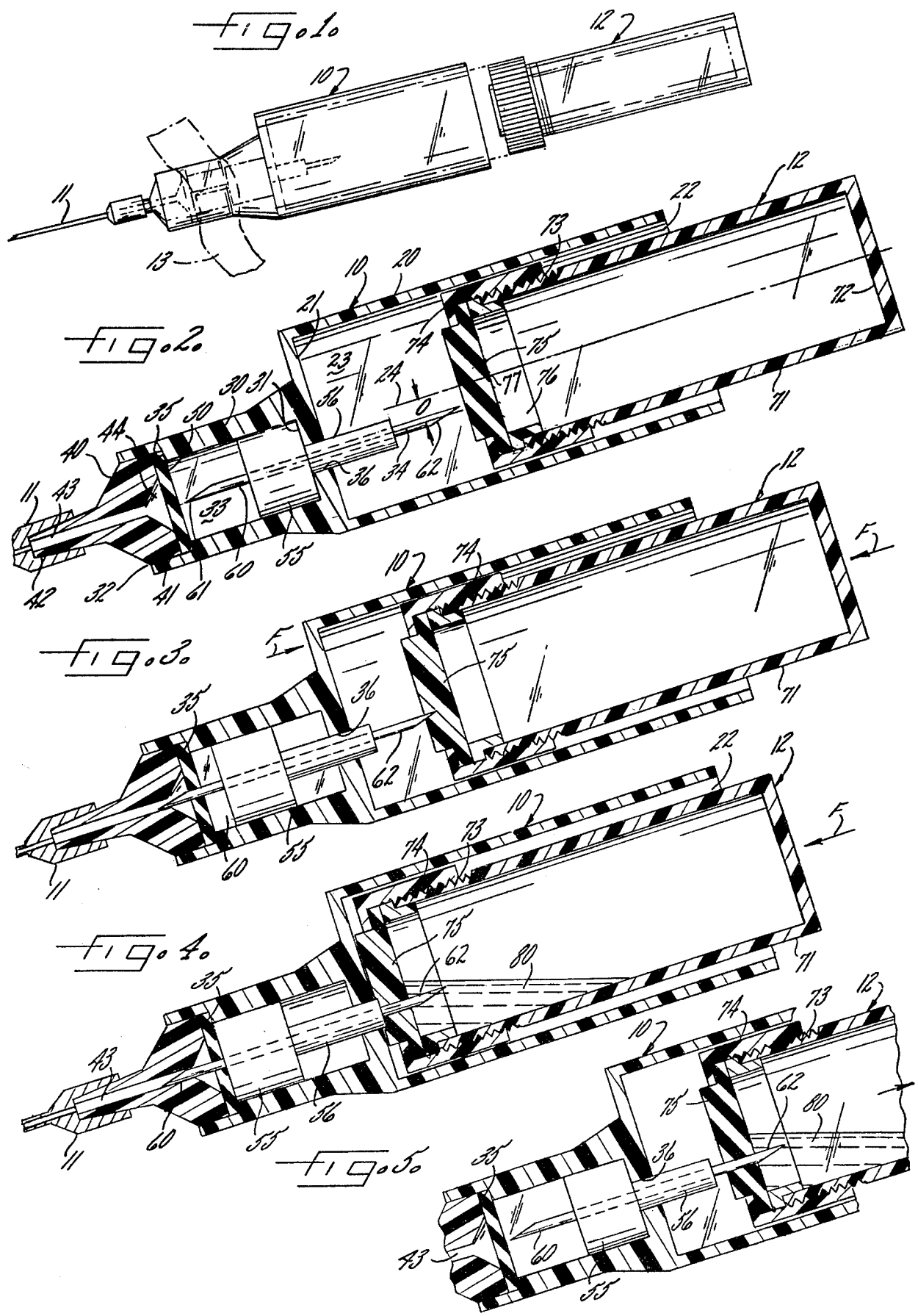

DEVICE AND PROCEDURE FOR COLLECTING A SUCCESSION OF INTRAVENOUS BLOOD SAMPLES

DESCRIPTION OF THE INVENTION

It has been recognized in the past that successive blood samples may be taken in evacuated vials through an intravenous needle which is taped in place on the patient, such evacuated vials being commonly referred to in the trade as "vacutainers". Such prior procedures have however been subject to a number of disadvantages. The carrier, normally of relatively large diameter, has been axially aligned with the intravenous needle which produces a "bad angle" for placement of the intravenous needle in a vein of shallow depth. Considerable force has been required to activate a vial, running the risk of dislodging the needle from the vein. A further problem with conventional sample-taking techniques is that there is no way of knowing whether the needle is in the lumen of the vein unless blood is actually seen to flow following application of vacuum. This problem is especially acute in the case of a patient with small, collapsed or deep set veins. Instead of the gentle trial and error available to the operator of a syringe, the only alternative, if the vein is not properly struck, is to probe again with a fresh vial, or series of vials, which is uncomfortable to the patient and wasteful of vials. Because of this "location" difficulty, present "vacutainer" techniques are completely unsuitable for arterial sampling.

Conventional stoppers, to be vacuum-tight, must be fitted tightly. Because of this, and because of residual vacuum, considerable force is required to remove them to expose the sample. Indeed, opening a vial is often somewhat violent resulting in loss of a portion of the sample and running risk of contaminating the handler as well as the surroundings. Notwithstanding the use of tightly fitted stoppers, conventional "vacutainers" are subject to leakage after they are removed from the evacuated tin in which they are shipped, and there is no way to tell whether leakage has occurred until actual usage.

Moreover, conventional "vacutainers" require rather expensive equipment for evacuation of the vials on a batch basis. Loosely capped vials are stacked in a chamber which is evacuated and the stoppers are then pressed home by gross movement of the upper wall of the chamber. Equipment capable of doing this must be expensive and heavily built.

Finally, conventional techniques employ a double needle, the outer end of which is provided with a laterally facing, normally sealed exit opening. Consequently the blood must undergo a sudden change of direction in flowing to the vial. The resulting turbulence inherently results in loss of blood quality.

It is, accordingly, an object of the present invention to provide a blood sampling device and procedure which avoids the above difficulties. It is, to begin with, an object to provide a carrier having a main chamber for receiving a vial but in which the main chamber is laterally offset to permit a more shallow angle of penetration of the intravenous needle.

It is another object to provide a blood sampling device which requires only a relatively light force to establish communication between the intravenous needle and the vial, thereby minimizing the likelihood that the intravenous needle will become dislodged from the vein incident to taking a sample.

It is a primary object of the present invention to provide a blood sampling device in which the technician has "proof positive" that the intravenous needle is properly located in the vein before attempting to apply an evacuated vial. Thus it is an object to provide a transparent "antechamber" in the sampling device at the upper end of the intravenous needle, the antechamber being small but nevertheless sufficiently large so as to admit a small quantity, or "trace", of blood by venous pressure alone and which forms a "telltale" to establish that the needle is in proper position in the vein and that an evacuated vial may be pressed into active receiving position. Thus it is an object of the invention to provide a blood sampling system which is more positive, in which a vein is "found" more quickly and with less discomfort to the patient, and which completely avoids the wastage of vials in abortive attempts at placement.

It is yet another object of the invention to provide a vial construction which avoids the use of the conventional pressed-in type of stopper which is often difficult to remove and which employs, instead, a threaded cap which may be as tight as necessary to avoid loss of vacuum but which may, nonetheless, be easily loosened and removed, without loss of the contents of the vial, when the sample is utilized.

It is still another object of the invention to provide a vial which is topped with a rubber diaphragm and which is evacuated by insertion of an evacuation needle through the center thereof but in which the auxiliary needle which admits the sample to the vial must necessarily penetrate the diaphragm at an off-center position thereby insuring sterility and penetration through a freshly made hole. Evacuation by means of a centrally inserted needle can be accomplished by evacuation equipment which is less complicated and expensive than that normally required.

Then too, it is an object to provide an evacuation device and procedure in which the blood flows from the intravenous needle through an auxiliary needle and into the evacuated vial in a "straight through" path, in which there are no bends in the stream, and in which turbulence is therefore reduced to a minimum thus insuring that there is no degradation in the quality of the sample.

It is a general object of the present invention to provide a blood sampling device and procedure which is more comfortable for the patient, which is quick and easy to use, and which is highly economical; indeed, the cost is so low as to permit the device to be furnished and used as a "disposable" item. Nevertheless, the device may, if desired, be sterilized for reuse without loss of reliability or operating characteristics.

Other objects and advantages of the invention will become apparent upon reading the attached detailed description and upon reference to the drawings in which:

FIG. 1 is a perspective view of a blood sampling device constructed in accordance with the invention showing placement of the intravenous needle at a shallow angle and showing an evacuated vial in readiness for insertion into active position.

FIGS. 2, 3 and 4 constitute a stop-motion series showing the sequential action of the double-ended auxiliary needle upon insertion, while FIG. 5 shows withdrawal.

While the invention has been described in connection with a preferred embodiment, it will be understood that I do not intend to be limited to the particular embodiment shown, but intend to cover the various alternative and equivalent constructions included within the spirit and scope of the appended claims.

Turning now to the drawings, there is shown a blood sampling device including a carrier 10 to which is secured an intravenous needle 11 and which is chambered for reception of an evacuated vial 12. The carrier is shown in FIG. 1 as taped in place on a patient with a length of adhesive tape 13 to hold the needle 11 in position in the lumen of a vein. Briefly stated, once the carrier 10 is in place, a blood sample is taken by simply pressing a vial 12 into seated position in the carrier, the vial being withdrawn when a sample of desired size has been achieved, the insertion and withdrawal of the vial in the carrier serving to make, and subsequently break, the fluid connections as will be discussed in greater detail. By use of a number of vials, blood samples can be taken either in quick succession or at separated intervals extending over a period of time, as desired.

Focusing the attention upon the carrier 10 (FIG. 2), it will be seen to include a relatively deep cylindrical cup 20 having a base 21 and an open outer end 22 and defining a main chamber 23 having a central axis 24. Formed integrally with the cup 20 is a second cup 30 having a base 31 and a mouth 32 defining a mid-chamber 33 having an axis 34. The mouth is annularly recessed to form a seat 35. The integral bases 21, 31 of the cups form a thin common barrier between them. Communication is provided through the barriers and between the chambers 23, 33 in the form of a clearance opening 36.

Seated in the recess is a fitting 40 having a base 41 and a tip in the form of a male connection 42 which is preferably tapered to standard "leur" dimension. The fitting 40 has a central passageway 43 which is enlarged, or relieved, at its inner end to provide an antechamber 44. The carrier 10, including the fitting 40, are preferably formed of transparent plastic such as polystyrene, so that any blood in the antechamber 44 will be immediately visible to the nurse or technician, serving as a telltale, as will be described.

In carrying out the invention, a soft easily penetrated rubber disc 50 is interposed between the mid-chamber 33 and the antechamber 44, the disc being captured around its edge between the seat 35 and the base 41 of the fitting 40.

Further in accordance with the invention, a piston 55 is mounted in the mid-chamber 33 for free sliding movement, the piston having an integral neck 56 which telescopes through the clearance opening 36. The piston has fixed therein an auxiliary double-ended needle 60 having an inner end 61 and an outer end 62, intended for sequential action in control of the flow, as will be described. Attention may first be given, however, to the construction of the vial 12 which forms a part of the present system.

The vial 12 is in the form of an elongated cup-shaped container having a cylindrical wall 71, and integral base 72 with a thread 73 at its open end. The thread is engaged by a screw cap 74 having a central opening and which holds captive, in the opening, a rubber diaphragm 75. Interposed between the cup and the diaphragm is an annular sealing element 76. The cap 74 and sealing ring 76 pinch the periphery of the rubber diaphragm 74 to seal the diaphragm effectively to the cup so that, once the vial is evacuated, there will be no inward leakage of air. It is one of the features of the construction that the tightly closed vial is evacuated, as a final step, by an evacuation needle which is thrust into the center of the diaphragm 75, leaving a self-sealing evacuation opening 77.

In a typical sampling procedure there are two phases, the first being the placement of the intravenous needle in the lumen of the vein and the second being the actual withdrawal of the sample. Using the present device the needle 11 is inserted in a position which is calculated to angularly intersect, and make communication with, a vein. The nurse or technician probes gently, keeping a close eye on the antechamber 44. The fact that the needle has been properly placed is indicated by immediate appearance of color in the antechamber, the color resulting from blood which has been forced up through the needle into the chamber by venous pressure. It is found that any small quantity of blood, even less than a drop, and referred to as a "trace", suffices to provide a reliable telltale. While the volume of the antechamber 44 is intentionally limited, nevertheless it is sufficiently large so that negligible back pressure is developed upon entry of a quantity sufficient to provide reliable indication. Once the vein has been "found", the carrier is temporarily taped in place as shown in FIG. 1.

As the next step in the procedure a pre-evacuated vial 12 is slid into the main chamber of the carrier as illustrated in FIG. 2. As the vial is lightly pressed into seated position, the outer end 62 of the auxiliary needle 60 is engaged by the rubber stopper or diaphragm on the vial, which causes the needle 60 and piston 55, together, to retreat so that the inner end 61 of the needle enters and fully penetrates the rubber disc 50 as illustrated in FIG. 3. This penetration of the disc requires minimal force because of the softness of the rubber which is employed. The result is to establish communication between the two needles. Upon continued inward movement of the vial, the piston 55 "bottoms" in the mid-chamber 33 so that the end 62 of the auxiliary needle, is sequence, penetrates the rubber diaphragm 75 on the vial, thus, as a final step, establishing communication between the auxiliary needle and the evacuated space so that blood is drawn into the vial, as illustrated in FIG. 4, under the influence of the vacuum, forming a pool 80. While penetration of the diaphragm 75 requires more force than penetration of the disc 50, the diaphragm is so chosen that the differential is small. And since balanced forces F (FIG. 3) may be applied between thumb and forefinger, very little "net" force is transmitted to the needle 11, so that there is little risk of dislodging the needle from its position in the vein.

When a sufficient quantity of blood has been collected in the vial, the vial is simply withdrawn axially by the fingertips while holding the carrier in position. This results in sequential sealing: In the first place the inner end of the auxiliary needle is withdrawn from the soft rubber disc, followed by bottoming of the piston 55 at its outer end (FIG. 5). Withdrawal of the auxiliary needle from the disc enables the disc to resiliently re-seal the penetration opening for positive cut-off of the flow.

Upon continued outward movement of the vial, the outer end 62 of the auxiliary needle is drawn clear of the rubber diaphragm 75 in the vial, which also re-seals itself, insuring a sterile sample.

If desired, a number of vials 12 may be filled in this fashion in quick succession permitting the carrier to be promptly untaped and removed. Alternatively the carrier may be left in its taped position for the collection of additional samples at some later time. The carrier may be left in place with minimal discomfort to the patient. As a still further alternative, the carrier may be removed and simply the needle 11 left in place.

One of the advantages of the invention accrues upon opening of a vial. Since a vial will have only a portion of the volume occupied by a blood sample, vacuum will still exist within the vial. Such vacuum, combined with the tightness of stoppering, has, in the past, made access to the sample difficult. In contrast, the present screw cap 74, particularly if a low pitch thread is used, may be easily twisted loose regardless of the amount of residual vacuum in the vial and regardless of the fact that it has been firmly tightened prior to initial evacuation. What has been, in the past, a risky and uncertain chore becomes now a matter of ease and predictability.

Moreover, since the screw cap is capable of developing higher forces at the sealing surfaces, the reliability of retention of vacuum is increased. Thus the inconvenience and wastefulness of leaky "vacutainers", once they have been removed from the shipping container, is avoided. However, in the event that one of the present vials 12 does lose its vacuum, the technician is immediately aware of this fact by reason of failure to draw blood even though blood is seen to exist in the antechamber, and a fresh vial may be substituted without any speculation as to whether the fault might lie in the venous connection.

It is one of the features of the present device that the axis 24 of the main chamber is laterally offset from the axis 34 of the mid-chamber, antechamber and the needles, the offset being indicated at "0" in FIG. 2. The degree of offset may, as a limiting condition, be such that the sidewalls 20, 30 of the chambers are, on one side, substantially flush with one another. This not only provides a "good" angle of insertion but insures that the outer end 62 of the auxiliary needle will penetrate the diaphragm at a point which is certain to be offset from the central evacuation opening 77. This insures sterility regardless of whether a single sample of blood is taken by the vial or whether a composite sample is taken, in the same vial, at timed intervals as may be desirable in certain procedures. The penetration of the diaphragm 75 at a point spaced from the axis has the further advantage that the thickness of rubber penetrated for evacuation may be different than the thickness penetrated for the taking of a sample. Thus the center portion of the diaphragm 75 may be centrally domed to increase the axial thickness and thereby improve the re-sealing capability after evacuation, while keeping the thickness at the radius of penetration of the auxiliary needle at a desired level which permits easy insertion and withdrawal of the vial while preserving sufficient differential, with respect to the disc 50, to insure the desired sequential action.

The fact that in the taking of the sample the blood flows "straight through" without having to make any 90° bends insures that the sample taken will be of high quality, free of the effects of turbulence.

It will be apparent to one skilled in the art that the construction has high inherent economy. The carrier may be easily molded in two pieces, shell and end fitting, using clear polystyrene plastic or the like, the two cup portions 20, 30 being integral with one another. The end fitting 40, which is also transparent and which is dimensioned for a press fit, serves to seal in the rubber disc 50 as well as to hold the piston 55, with its auxiliary needle, in captive position. The manufacturing cost of such a simple assembly is sufficiently low as to encourage disposable usage. The only change in the construction which might be indicated if the device is intended for re-use is the making of the end fitting 40 removable for cleaning purposes, such removability being readily obtained by use of a threaded connection rather than a press fit.

It is to be noted that in the preferred form of the construction the mid-chamber 33 acts as a longitudinal passageway from the main chamber to the soft rubber disc, the diameter of the passageway being such as to accommodate the diameter of the piston 55 and with the length of the passageway being such as to define limit stop surfaces. It will be appreciated by one skilled in the art that the invention, in its broader aspects, is not limited to a piston 55 having the proportions shown and the passageway 33 may be reduced in diameter as much as desired, in a limiting case to a diameter which only slightly exceeds that of the needle, with suitable limit stops being provided to limit the degree of excursion of the auxiliary needle, on the one hand to prevent overpenetration of the rubber disc 15 and on the other hand to prevent the needle from being completely withdrawn.

Referring to the disc 50, it will be understood that the term "disc" has been used for convenience and that the invention may be practiced even though the element is of non-circular outline. The term "rubber" includes rubber-like materials. Similarly the term "plastic" shall be deemed to include other materials having similar physical characteristics, as may be convenient.

The utility of the present device has been explained in connection with withdrawal of samples from a vein, and particularly a shallow vein. The device is, however, eminently well suited for drawing blood samples from deep-set arteries, using a gentle probing action until a show of color appears, constituting positive proof that connection has been made to the artery so that a vial may be pressed into receiving position with confidence, a feat which is not possible using ordinary techniques.

I claim:

1. In a blood sample collection system for use with an intravenous needle, the combination comprising a preevacuated vial having an extensive rubber cap, a carrier in the form of a large cylindrical cup defining a main chamber and a small cylindrical cup defining a midchamber, the cups having their mouths facing in opposite directions and being integral with one another base-to-base to form a thin common barrier between them and with their axes parallel and offset from one another to a degree that adjacent portions of the sidewalls thereof are substantially flush, the cups communicating via a clearance opening through the barrier and which is axially aligned with respect to the axis of the small cup, a readily-penetrated soft rubber disc at the mouth of the small cup, an end fitting secured to the mouth of the small cup adjacent the rubber disc for coupling to the intravenous needle and having an axial passageway formed therein, the end fitting being formed of transparent plastic and the axial passageway being relieved to form an antechamber immediately adjacent the rubber disc for reception of a trace of blood under venous pressure as a preliminary visual telltale that the lumen of the vein has been penetrated, a piston fitted for sliding movement endwise in the mid-chamber between limit positions, the piston having an auxiliary double-ended needle axially mounted therein and projecting from the ends thereof one end of which extends through the clearance opening in the common barrier and the other end of which is positioned for penetration of the soft rubber disc, the large cylindrical cup slideably receiving said vial with the rubber cap positioned for penetration by the one end of the auxiliary needle so that when the vial is pressed in, cap-first, the auxiliary needle first penetrates the soft rubber disc to establish communication with the intravenous needle and then penetrates the rubber cap on the vial in a random eccentric position to establish communication between the vial and the intravenous needle for the drawing of a sample of blood into the vial, and with the auxiliary needle being drawn from the rubber disc and then from the cap for resealing of the same when the vial is subsequently removed.

2. The combination as claimed in claim 1 in which the cap is threaded on the vial, the cap having a central rubber diaphragm occupying a substantial portion of the vial diameter thereby insuring insertion of the diaphragm by the auxiliary needle in all eccentric positions of insertion of the vial into the main chamber, the diaphragm having a thickness in all said eccentric positions which is the same and which is only a fraction of the diameter thereof.

3. The combination as claimed in claim 2 in which the cap has an annular internal seat defining an extensive central opening, the diaphragm being retained by the seat to occupy the opening, and a sealing ring interposed between the mouth of the vial and the diaphragm to press the latter against the seat to provide a positive seal when the cap is tightened, the thread being sufficiently shallow as to permit subsequent opening with only light manual twisting force.

* * * * *